United States Patent
Harder

[11] Patent Number: 5,968,048
[45] Date of Patent: Oct. 19, 1999

[54] BORE HEAD FOR BORING BONE CHANNELS

[75] Inventor: Hans Erich Harder, Probsteierhagen, Germany

[73] Assignee: Howmedica GmbH, Germany

[21] Appl. No.: 09/000,070
[22] PCT Filed: Jul. 22, 1996
[86] PCT No.: PCT/EP96/03230
§ 371 Date: Jan. 22, 1998
§ 102(e) Date: Jan. 22, 1998
[87] PCT Pub. No.: WO97/03617
PCT Pub. Date: Feb. 6, 1997

[30] Foreign Application Priority Data

Jul. 22, 1995 [DE] Germany ............ 295 11 872 U

[51] Int. Cl.$^6$ .................................................. A61B 17/56
[52] U.S. Cl. .................................................. 606/80
[58] Field of Search .................... 606/80, 79, 85, 606/104, 73

[56] References Cited

U.S. PATENT DOCUMENTS

| | | | |
|---|---|---|---|
| 3,554,192 | 1/1971 | Isberner | 606/80 |
| 5,122,134 | 6/1992 | Borzone et al. | 606/80 |
| 5,180,384 | 1/1993 | Mikhail | 606/80 |
| 5,190,548 | 3/1993 | Davis | 606/80 |
| 5,514,141 | 5/1996 | Prizzi, Jr. | 606/80 |
| 5,720,749 | 2/1998 | Rupp | 606/79 |

FOREIGN PATENT DOCUMENTS

| | | |
|---|---|---|
| 440371 | 8/1991 | European Pat. Off. . |
| 508710 | 10/1992 | European Pat. Off. . |
| 219479 | 7/1924 | United Kingdom . |

*Primary Examiner*—Guy V. Tucker
*Attorney, Agent, or Firm*—Lerner, David, Littenberg, Krumholz & Mentlik, LLP

[57] ABSTRACT

Drill head for boring out bone channels, characterized by the following features:

a central bore for a guide wire;

four spiral teeth arranged at 90% intervals on the periphery and having a small angle of twist, such as 15°, that form an angle of approximately 45% relative to the longitudinal axis of bore at the forward end in the starting cut and that form the main cutting edges and whose secondary cutting edges consecutive to the main cutting edges are located approximately on a cylinder whose axis coincides with the axis of the bore, the length of the secondary cutting edges located on the cylindrical surface is smaller than the diameter of the cylinder;

the rounded base of the slot-like chip chambers between the teeth is radially close to the bore and the faces of the teeth bordering the chip chambers in the starting cut area are provided with a ground face such that a relatively sharp edge is formed, extending from the ends of the teeth and the chip chamber surfaces between them to the bore.

7 Claims, 1 Drawing Sheet

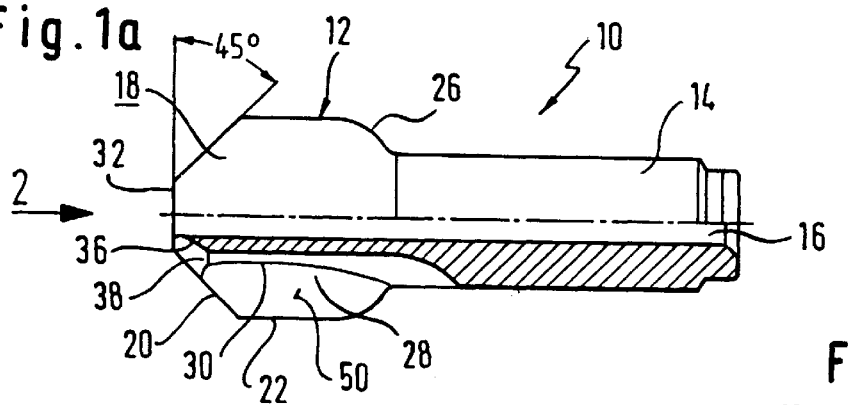
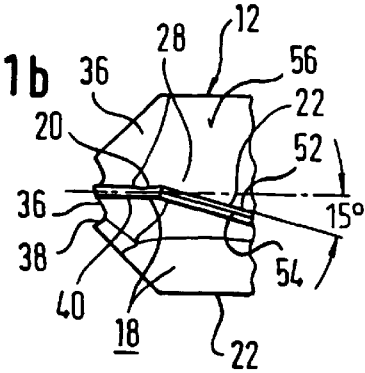
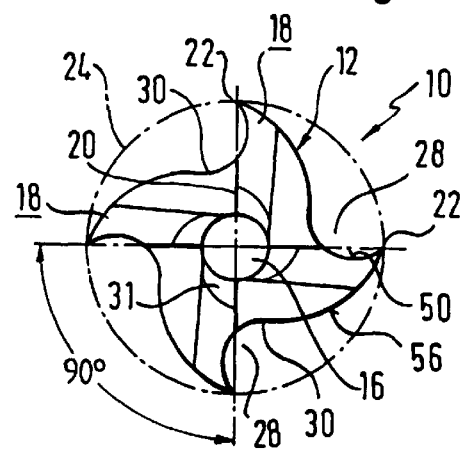
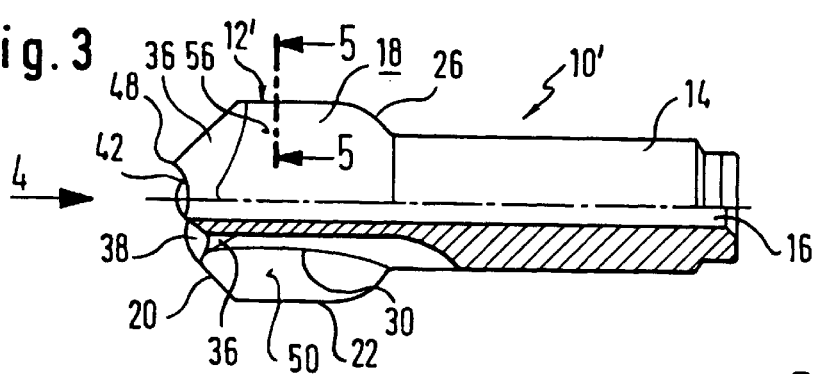
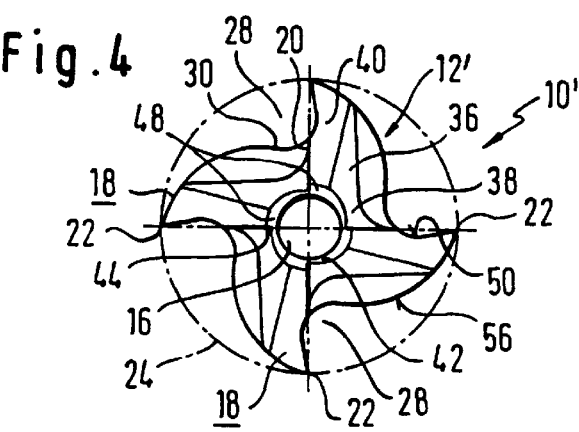
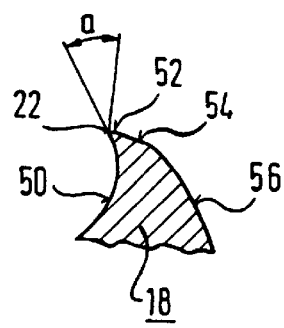

BORE HEAD FOR BORING BONE CHANNELS

This application is filed under 35 USC 371, based on PCT/EP96/03230 filed on Jul. 22, 1996.

The invention concerns a reaming tool for boring out bone channels.

Especially before inserting implants in long tubular bones, the bone channels are first bored out so the implant can be inserted or driven into the channel. In most cases, this boring is done with a twist drill head having a relatively short shank that can be connected to a flexible drive shaft and is driven to rotate by a suitable drive mechanism. The flexible drive shaft and the drill head have a continuous bone. It accommodates a guide spike that has previously been tapped into the bone. This provides guidance for the drill head and prevents it from penetrating through the bone wall at the side.

In boring out bone channels, there is the danger of unnecessary injury. Especially when the pressure and temperature in the medullary space rise sharply, there is also the danger of a fat embolism, which must be prevented in any case.

A reaming tool is known from EP-A-0 440 371, the drill head of which comprises a row of twisted teeth which from chip chambers in between. The teeth are rounded concerning their outer contour, by which only the middle area between the ends effects cutting. The drill head is joined with a flexible shank which works as a flexible shank. From the same document reaming tool is known which comprises a row of teeth at the drill head which run off in a first cutting section and form the main cutting edges in this area. The secondary cutting edges are straight and are lying on a cylinder, the axis of which coincides with the axis of the drill head.

A reaming tool of the above mentioned kind is known from the EPA 0 508 710. It comprises four teeth arranged as 90° intervals on the periphery having a starting cut in which the main cutting edges are formed. The secondary cutting edges are lying on a cylinder the axis of which coincides with the bore. The length of the secondary cutting edges is smaller than the diameter of the cylinder. The known drill head is joined with a solid shank and above all serves for boring out small lengths in the bone.

The object of the invention is to create a reaming tool for boring out bone channels such that it will permit a relatively rapid advance, plus good chip flow, and a low pressure at the same time.

This object is achieved according to this invention through the features of claim 1.

The drill head according to this invention has four spiral teeth, each having a small angle of twist, arranged with 90° intervals between them around the circumference. For example, the angle of twist may be in the range of 15°. The starting cut has an angle of approximately 45° (angle of point 90°). It has been found that such a starting cut is especially advantageous.

The secondary cutting edges are located on the outside of the teeth approximately on a cylinder the axis of which coincides with the axis of the bore. The secondary cutting edges thus run approximately on a straight line that is approximately the same distance from the axis along its entire length. Such a design of the teeth permits good guidance in the bone canal independently of the guide spike. This eliminates the danger of the drill head cutting too far into the bone wall on the side.

Another feature of this invention is that the base of the chimp chamber between the teeth or chip groove is very close to the bore. Only enough material is left for the drill head to have sufficient stability. For example, the base of the chip chamber may be located at a radial distance from the axis of the bore which corresponds approximately to the outside radius of the shank of the drill head. However, it is also conceivable for the base to the shank is created so there is no congestion of chips. The relatively larger chip chambers created in this way permit excellent chip removal.

Finally, a ground surface is created according to this invention on the faces adjacent to the chip chambers in the area of the starting cut such that a relatively sharp edge is formed, extending from the ends of the teeth and the chip chambers between them to the bore. This feature means that the starting cut is sharpened or pointed, which permits effective penetration and cutting into the bone channel, even when the medullary canal is narrow.

Since there is a risk that the guide spike might damage the sharp edge formed in the bore, one embodiment of this invention provides for the bore to have a countersunk area in the forward end. This permits a certain tilting due to tolerances between the drill head and the guide spike without any damage to the edge, which remains sharp.

According to another embodiment of this invention, the outside contour of the teeth is provided with a curvature at the rear end which then comes in contact with the shank of the drill head. The radius of curvature is relatively large to prevent undercutting when drilling in the channel.

The length of the secondary cutting edge, which is located on a cylindrical surface, as described above, must not be too large because then there would be the risk of blockage. Therefore, the length of this cutting edge is smaller than the diameter of the cylinder in any case.

The effective cutting angle on the cutting edges is preferably in the range of 20° to 22°. In one embodiment of this invention, the face is formed by a concave face that extends to the ground face. Together with the relatively deep chip chamber, this yields the desirable effect that bone material is scraped out while chips are removed well at the same time.

According to another embodiment of this invention, the clearance angle is approximately in the angle of 13° to 17°, and two flanks with different angles can be connected to the secondary cutting edges. For example, the first flank adjacent to the cutting edge may have an angle of 13° to 15°, while the adjacent flank may have an angle of 15° to 17°.

This invention is explained in greater detail below with reference to the Figures.

BRIEF DESCRIPTION OF THE DRAWINGS

FIG. 1a shows a drill head according to this invention, partially in side view and partially in a sectional view and also partially before the last finishing operation.

FIG. 1b shows part of the drill head of FIG. 4 in side view.

FIG. 2 shows an end view of the drill head according to FIG. 1 in the direction of arrow 2, although only formation of the upper half is shown, i.e. before last manufacturing step.

FIG. 3 shows a diagram similar to that in FIG. 1, but after the final finishing.

FIG. 4 shows an end view of the drill head according to FIG. 3 in the direction of arrow 4.

FIG. 5 shows a section through a tooth of the drill head according to FIGS. 1 to 4 in the outer radial area.

DETAILED DESCRIPTION OF THE PREFERRED EMBODIMENT

Tool 10 illustrated in FIG. 1 consists of the actual drill head 12 and a cylindrical shank 14. Shank 14 and head 12 are designed with a continuous central bore 16, only the lower half of which is illustrated in FIG. 1. The bore may have an inside diameter of 3.6 mm, for example.

It should be pointed out that the top half of FIG. 1 shows an intermediate stage of processing, while the lower half shows the final stage of processing.

Drill head 12 has four teeth 28 arranged at 90° intervals and extending radially outwards and having a main cutting edge 20 with an angle of 45° relative to the longitudinal axis (FIG. 1) in the area of the starting cut. Secondary cutting edges 22 of teeth 18 are located on the surface of a cylinder whose axis coincides with the axis of bore 16. Such a cylinder is indicated with dash-dot lines 24 in FIG. 2. The teeth have a slight twist of approximately 15°, for example (FIG. 1b). At the rear end, the transition from the contour of the teeth to the shank has a curvature as indicated by 26. Curve 26 has a relatively large radius.

Chip chambers 28 are formed between teeth 18 and have a base 30 that is designed with a relatively small radius and is radially relatively close to bore 16, in other words, material thickness between ground 30 and bore 16 is rather small. The chip chambers therefore have a relatively large cross section so they can accommodate and remove more chips.

In fabrication, drill head 12 is first provided with four ring face sections 32 at the tip that, equally spaced, surround the axis of the bore 16 in the area of the forward end of teeth 18 almost vertical to the longitudinal axis. However, these face sections 31 would cause too much resistance when the drill head is advanced in medullary canal and thus would cause too much pressure. Therefore, a ground face is created in the facing surfaces of teeth 18 of a chip chamber 18, as shown by the lower half of FIG. 1 and FIGS. 3 and 4. A ground face 36 with a large area is created on the rear face of each tooth 18 in the starting cut area. It leads to sharpening of the starting cut area, because the face 36 has a larger angle to the longitudinal axis than the rest of the back side of teeth 18. On the from side a further respective ground face 38 on the front end of teeth 18 is relatively small in area. Both round faces 36, 38 lead to a reduction in the width of flank 40 of the teeth in the starting cut area, as shown in FIG. 4. Ground faces 36, 38 are positioned in such a way as to form on the whole a "tip" on drill head 12 in the starting cut area with the design of an almost linear sharp edge 42 of the front end of the bore 16. However, since the sharp edge runs the risk of being damaged by a guide spike that is inserted through bore 16, a countersunk area 44 is provided at the end of bore 16, so that play between drill head 12 and the guide spike need not necessarily result in damage to sharp edge 42. The ground face 36, 38 and the countersunk area 44 lead to the result that the forward ends of teeth 18 project outward in the area of the starting cut, as indicated by 48, while the edge 42 between the prongs 48 is located farther back with a curve between them (FIG. 3). This yields a cutting effect in use.

To illustrate the difference between FIGS. 1 and 2 and FIGS. 3 and 4, the tool in FIGS. 3 and 4 is designated as 10' and the drill head is labeled as 12'.

FIG. 5 shows a section through a tooth 18 in the area of secondary cutting edge 22. This shows that face 50 is designed as a concave surface. The effective cutting angle a is about 20° to 22° the flank on secondary cutting edge 22 is subdivided into a first flank section 52 of very low width (see FIG. 1b) and a little wider second flank section 54. The first has a clearance angle of about 13° to 15° and the second has a clearance angle of 15° to 17°. This is adjacent to the spiral rear face 56 of tooth 18. The effective cutting angle of main cutting edge 20 is similar to effective cutting angle a.

I claim:

1. A drill head for boring out bone channels comprising:

(a) a central bore for a guide spike;

(b) four teeth arranged at 90° intervals on the periphery, which from main cutting edges being angular to the longitudinal axis of bore and secondary cutting edges adjacent to the main cutting edges, wherein the teeth are in form of a screw line having a small angle of twist;

the main cutting edges have an angle of 45° to the longitudinal axis of the bore, chip chambers are between the teeth formed slot-like having a curved ground being radially close to the bore and leaving only enough material for providing sufficient stability, and faces of the teeth bordering the chip chambers are provided with a ground face extending from the frontward ends of the teeth and the chip chamber surfaces between them to the forward end of the bore.

2. The drill head according to claim 1, wherein the bore has a countersunk area on the forward end.

3. The drill head according to claim 2, wherein the outside corner of the teeth has a curvature toward the clamping shank on the rear end.

4. The drill head according to claim 3, wherein the faces comprise a continuous concave surface extending to the ground face.

5. The drill head according to claim 4, wherein a first flank adjacent to the secondary cutting edge has a smaller width and forms a first clearance angle, and the second flank adjacent to the former has a larger second clearance angle.

6. The drill head according to claim 5, wherein the ground faces are planar.

7. The drill head according to claim 6, wherein the radius of the ground of the chip chambers is less or equal to the outer radius of the shank having an according transition from chip chamber to shank.

* * * * *

UNITED STATES PATENT AND TRADEMARK OFFICE
CERTIFICATE OF CORRECTION

PATENT NO. : 5,968,048
DATED : October 19, 1999
INVENTOR(S) : Harder

It is certified that error appears in the above-identified patent and that said Letters Patent is hereby corrected as shown below:

In the Abstract:
 line 4, "90%" should read --90°--;
 line 6, "45%" should read --45°--.

Column 1, line 24, "from" should read --form--.
Column 1, line 29, after "document", insert --a--.
Column 1, line 30, "run" should read --runs--.
Column 1, line 31, "form" should read --forms--.
Column 1, line 67, "chimp" should read --chip--.
Column 2, line 6, after "base" insert --to be located even closer to the bore if an appropriate transition from the chip chamber--.
Column 3, line 31, after "in", insert --a--.
Column 3, line 40, "round" should read --ground--.
Column 3, line 51, "face" should read --faces--.
Column 4, line 19, after "of", insert --the--.
Column 4, line 33, "forward" should read --frontward--.

Signed and Sealed this

Fifteenth Day of August, 2000

Attest:

Q. TODD DICKINSON

*Attesting Officer*       *Director of Patents and Trademarks*